United States Patent [19]

Glazer et al.

[11] Patent Number: 5,582,793

[45] Date of Patent: *Dec. 10, 1996

[54] PROCESS FOR TREATING WASTE MATERIAL

[75] Inventors: Sanford A. Glazer, Potomac, Md.; Robert S. Russell, Orlando, Fla.; Bernard M. Cole, Northbrook, Ill.

[73] Assignee: Antaeus Group, Inc., Hunt Valley, Md.

[*] Notice: The term of this patent shall not extend beyond the expiration date of Pat. No. 5,277,869.

[21] Appl. No.: 413,853

[22] Filed: Mar. 29, 1995

Related U.S. Application Data

[63] Continuation-in-part of Ser. No. 179,721, Jan. 11, 1994, Pat. No. 5,427,737, which is a continuation-in-part of Ser. No. 8,870, Jan. 25, 1993, Pat. No. 5,277,869, which is a continuation of Ser. No. 772,094, Oct. 3, 1991, abandoned.

[51] Int. Cl.⁶ .................................................. A61L 2/06
[52] U.S. Cl. .......................... 422/26; 422/28; 241/17; 241/23; 241/606; 241/65
[58] Field of Search ........................ 422/26, 32, 33, 422/38, 105, 108, 184, 286, 287, 307, 309, 28; 241/606, 15, 17, 23, 46.17, 65; 588/258, 900

[56] References Cited

U.S. PATENT DOCUMENTS

| | | | |
|---|---|---|---|
| 3,589,276 | 6/1971 | Swallert | 100/90 |
| 3,762,874 | 10/1973 | Berry | 422/28 |
| 4,037,795 | 7/1977 | Fyfe | 241/58 |
| 4,623,515 | 11/1986 | Frei et al. | 422/1 |
| 4,905,916 | 3/1990 | Sorwick et al. | 241/23 |
| 4,917,310 | 4/1990 | Carrera | 241/32 |
| 5,035,367 | 7/1991 | Nojima | 241/37.5 |
| 5,048,766 | 9/1991 | Gaylor et al. | 241/65 |
| 5,077,007 | 12/1991 | Pearson | 422/3 |
| 5,087,420 | 2/1992 | Jackson | 422/37 |
| 5,089,994 | 2/1992 | Meijer | 422/37 |
| 5,119,994 | 6/1992 | Placzek | 241/17 |
| 5,186,397 | 2/1993 | Orlando | 241/23 |
| 5,217,688 | 6/1993 | Von Lersner | 422/26 |

FOREIGN PATENT DOCUMENTS

| | | |
|---|---|---|
| 0054823 | 6/1982 | European Pat. Off. . |
| 3705823 | 5/1988 | Germany . |
| 7-108532 | 4/1995 | Japan . |
| WO90/14890 | 12/1990 | WIPO . |

*Primary Examiner*—Robert J. Warden
*Assistant Examiner*—Theresa T. Snider
*Attorney, Agent, or Firm*—Venable, Baetjer, Howard & Civiletti

[57] ABSTRACT

A process and processing system are disclosed that provide for the processing of many forms of waste, such as medical waste, food waste disposable diapers or the like, that both reduces the volume of waste solids and neutralizes the biological activity of such waste, thereby facilitating the disposal of potentially unhealthy or hazardous materials. The process and system also provides for the removal of coating from the surfaces of plastic waste material or for the dissolution of water soluble polymeric or fibrous waste material. Biological neutralization or, alternatively, coating removal or dissolution of water soluble waste, is accomplished by chopping the waste material and mixing it with a circulating stream of fluid such as water that is heated to a temperature which effects disinfection or sterilization or, alternatively coating removal or waste dissolution, in accordance with the needs of the user. The heated fluid is maintained substantially in a liquid form to facilitate intermixing with the waste material and absorption thereby in instances of the processing of fluid-absorbable materials. The processed waste can be filtered to remove solid particles having a size in excess of a predetermined amount, and the filtrate can be passed into municipal sewer systems. The filtered solids can be disposed of in a conventional manner, as by disposal in land fills, burial, or incineration.

17 Claims, 10 Drawing Sheets

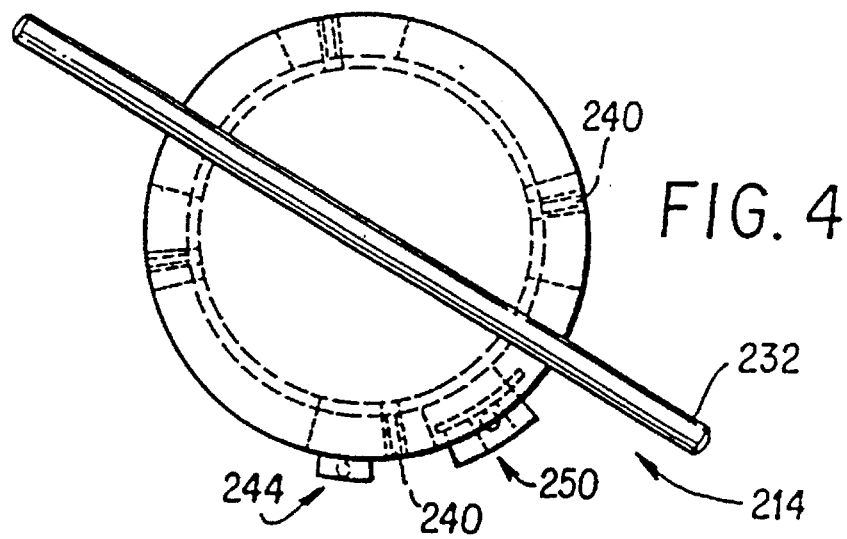
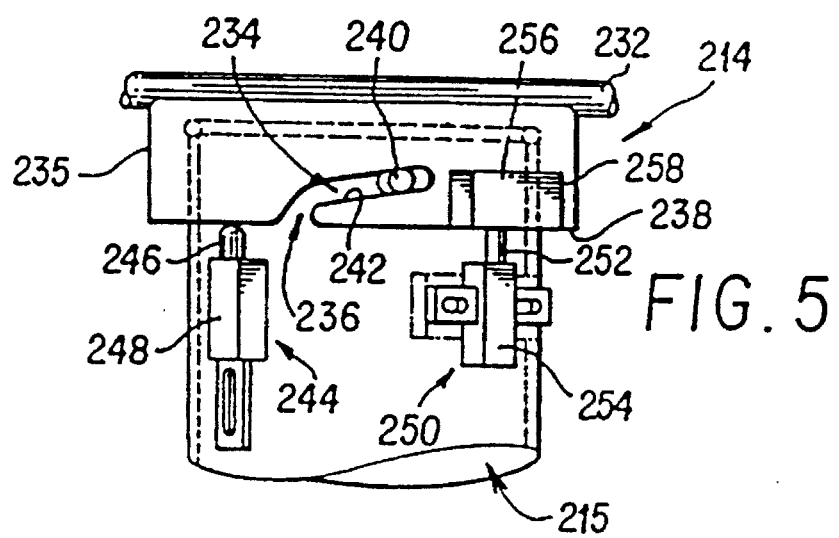
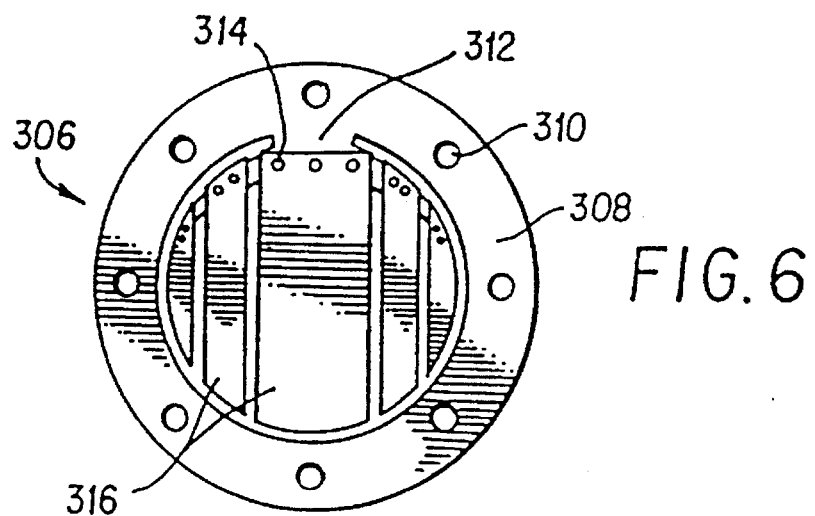

PROCESS FOR TREATING WASTE MATERIAL

This application is a continuation-in-part of application Ser. No. 08/179,721, filed on Jan. 11, 1994, now U.S. Pat. No. 5,427,737, which in turn is a continuation-in-part of application Ser. No. 08/008,870, filed on Jan. 25, 1993, now U.S. Pat. No. 5,277,869. Application Ser. No. 08/008,870 is a continuation of patent application Ser. No. 07/772,094, filed on Oct. 3, 1991, now abandoned.

BACKGROUND OF THE INVENTION

The invention relates generally to waste disposal methods and apparatus, and more particularly to methods and apparatus for effecting disinfection, and optionally sterilization, of waste material such as medical, food, disposable diapers and other types of waste, and for reducing the volume of such waste material, for removing coatings from waste coated plastic material, and for disposal of water soluble polymeric or fibrous waste material.

Waste management has evolved in the latter part of the twentieth century into an industry of considerable importance, as societal and environmental attention has focused on the conventional processes by which waste has to date been handled for disposal. These conventional waste disposal processes include incineration, dumping at sea, and burial in landfills. Each of these processes, however, is encumbered by significant societal and environmental disadvantages. Incineration is objectionable due to its attendant chemical and particulate pollution of the atmosphere and surrounding locales. Further, these pollutants can be transported over great distances by prevailing winds, thereby extending the scope of environmental impact beyond the immediate locale of the incinerator. Waste disposal in the oceans is objectionable due to its adverse environmental impact on sea lift and coastal shores. Landfills are objectionable due to their attendant spatial demands, offensive odors, and potential for production of hazardous substances arising from the mixing and interaction of buried materials. Spatial considerations are especially prevalent in urban centers, where population growth has resulted in suburban expansion to locations well outside of the urban center, necessitating in some instances in the relocation of existing landfills and the creation of costly new landfills at locations geographically remote from the centers they serve. Disposable diapers have proven to be an increasing problem for municipal disposal.

Additional waste disposal problems arise in view of the type of waste that is to be disposed. For example, special precautions are required for the disposal of biological and medical waste due to the overwhelming concern for preventing the creation and/or spread of infectious disease. Further concerns arise due to the presence of extremely sharp medical instruments such as needles, knives, and broken glass containers that can cut or lacerate the skin of personnel and animals with which the waste comes in contact, thereby presenting both a risk of physical harm and biological contamination. For these reasons, such waste is typically thermally or chemically treated and buried in dedicated medical waste disposal facilities. The treatment can be of a type that results in disinfection, and optimally sterilization, of the waste so as to render it biologically neutral or inert. As used in the description which follows, the term "disinfection" and its variants pertains to the destruction of pathogenic microorganisms or their toxins or vectors, whereas "sterilization" and its variations pertains to the destruction of all living microorganisms and their spores, thereby rendering the material so processed void of all living matter.

Sterilization can typically be accomplished by any one of a variety of prescribed chemical and non-combustion thermal treatment regimens, as well as incineration. Chemical sterilization generally provides for exposure of the waste material to an antiseptic solution such as liquid chlorine for a prescribed time interval; however, the use of chemical sterilizing agents presents disposal problems for the liquid following waste treatment due to the toxicity of chlorine and other antiseptic solutions. A popular alternative to chemical disinfection is autoclaving, which provides for exposure of the waste to heat at upwards of 250° F. (121° C.) at 15 psi for 15–40 minutes. While sterilization can be accomplished in both dry air and steam environments, steam autoclaving is generally preferred due to its greater penetrating capabilities (especially important for sterilizing "soft" waste such as textiles and gauze) and its lethality via the process of denaturation. Longer periods are used to assure steam penetration of heavy, fluid-absorbable loads. Faster processing can be accomplished for some waste materials by increasing temperature and pressure. However, a significant disadvantage of steam autoclaving is its failure to assure complete penetration of the waste and its exposure to the heat contained within the water vapor. Further disadvantages include the tendency for autoclaves (both steam and dry) to stratify and to trap comparatively cool air in pockets, thereby precluding sterilization. In addition, the waste is neither reduced in volume or in mass; instead, mass can increase in some instances (i.e., textiles and gauze) due to the absorption of water vapor, thereby exacerbating the problem of waste disposal referenced above.

In view of the foregoing, there is a pressing societal need to not only reduce the volume of waste material that is produced, but also to more effectively and efficiently process the waste so that it has a diminished environmental impact. The need is especially pressing in instances where waste is produced in bulk, as can occur in hospitals, nursing homes, restaurants and the like. While efforts are being undertaken to reduce waste production, these efforts alone will not eliminate the various problems associated with waste disposal, particularly in the medical and dental industries, where single patient use (i.e., non-reusable) surgical instruments have gained widespread acceptance due to concerns over spread of the family of hepatitis viruses and HIV. Accordingly, the present invention is directed to providing methods and apparatus for disinfecting, and optimally sterilizing, medical and other forms of waste, particularly when such is in bulk form and reducing the volume of waste solids for disposal. The present invention is also directed to providing methods and apparatus for removing coatings from waste coated plastic materials. The invention is further directed to providing methods and apparatus for treating water soluble polymeric or fibrous waste material. These and other objects and advantages of the present invention will become apparent from the following specification when read in conjunction with the accompanying drawings.

SUMMARY OF THE INVENTION

The invention is directed to methods and apparatus for disinfecting, and optimally sterilizing, non-toxic waste and for reducing the volume of waste solids, thereby simplifying procedures for waste disposal and reducing the demand for disposal space in landfills. While the invention is particularly advantageous for use in processing bulk medical waste in the form of aggregate or "red-bagged" medical waste along with non-aggregate medical waste, its principles are equally applicable for the treatment of other forms of waste, such as food waste produced incident to the operation of restaurants and so-called "fast food" establishments. The invention can also be used for processing disposable diapers. In this latter regard, waste treatment in accordance with the teachings of the present invention greatly reduces the organic content of the waste solids, thereby resulting in a diminution of rodent and other pest infestation typically associated with food waste disposal as well as the capacity requirements for waste receptacles (i.e., "dumpsters") onsite at the restaurant. Alternatively, the principles of the invention may be applied to the treatment of waste coated plastic material, whereby treatment results in the removal of substantially all coating from the surface of waste coated plastic material. In addition, the principles of the invention may be applied to the disposal of water soluble polymeric or fibrous waste materials, whereby treatment results in the dissolution of the waste material.

In one aspect of the invention, a closed, and optionally pressurized, waste processing system is provided that is operable to effect biological neutralization of waste by a process of waste sterilization. As used herein, the term "system" includes both methods and apparatus for effecting the desired form of waste treatment. The system provides for receipt of the waste in a decontamination chamber which is sealable by a removable cover. A pressurizable cover is used in instances where a pressurized processing system is employed. A reservoir can optionally be provided that is operable through appropriate valve apparatus to deliver water or other suitable fluids to the flow of waste material as it is drawn toward a waste processing chopper/pump assembly positioned downstream from the decontamination chamber. Alternatively, fluid can be supplied from a supply line such as a water or steam line. Preferably, the fluid is water and is stored within the reservoir at an elevated temperature of on the order of about 170° F. (77° C.) so as to expedite processing. However, the principles of the present invention are applicable for other liquids, such as various vegetable oils such as corn oil, mineral oils and synthetic oils, each having boiling points at temperatures in excess of 270° F., red preferably in the range of at least 300° F. to 450° F. The use of an oil for the fluid can be advantageous in the present invention, for such allows for operation of the system at elevated temperatures in the absence of pressurization, thereby avoiding altogether the complexity and expense that is associated with the construction of pressurized systems. A selectively-actuable gate can be provided in the line between the decontamination chamber and the chopper/pump to inhibit the flow of waste solids to the chopper/pump until it attains its optimal operating speed, at which point the gate can be opened to permit the fluid and solids stored in the chamber to flow to the chopper/pump for processing thereby. Output from the pump is directed to the decontamination chamber and circulates therethrough in a closed, pressurized circuit in a continuous manner, during which time the waste solids are ground by the chopper/pump to successively finer particles and mixed with the circulating fluid from the reservoir. Suitable heating apparatus is associated with the decontamination chamber to provide for heating of the fluid and entrained waste solids to the requisite temperature that is necessary to effect disinfection or sterilization as these materials are circulated by the pump for the desired period of time. Such heating apparatus can include, by way of example, an arrangement of one or more resistance heaters that are mounted along the exterior of the decontamination chamber, as well as a surrounding sleeve or jacket for retaining steam or another suitable fluid that is capable of transferring the requisite quantity of thermal energy to the decontamination chamber to elevate the temperature of the chamber contents to a prescribed temperature. Sterilization can be implemented by elevating the temperature of the circulating waste and fluid mixture to a temperature of at least 270° F. (132° C.) and maintaining that temperature for a time interval of at least six minutes. Temperature sensors are preferably provided along the fluid flow path to provide an indication of circulated fluid temperature throughout system operation and to ensure that the requisite processing temperature has been maintained for the required time interval.

Once the waste material has been ground by the pump and exposed to the heated water for the prescribed period of time, the water and entrained waste particulate are cooled to a prescribed minimum temperature so as to permit for disposal of the liquid portion of the mixture into the municipal waste disposal system. Cooling of the processed waste can be expedited by introducing a flow of cool water into the circulating stream of sterilized waste material or by surrounding one or more of the conduits through which the processed waste travels with a suitable heat exchanging medium or device. Although waste that receives a cool water flow will no longer be "biologically neutral" following its mixture with the tap water, the waste material will nevertheless be biologically and physically safe for disposal, as it will have a biological activity attributable only to that of the tap water with which it is mixed. Alternatively, the processed waste can be dried prior to cooling to further reduce waste volume. The grotrod waste solids can be filtered from the processed waste, compacted and disposed of in a conventional manner, whereas the waste liquids can be passed (following cooling) into the municipal sewer lines.

In a further aspect of the invention, waste processing in the foregoing manner is electronically controlled in accordance with a pre-established system program. However, variables such as pump speed, fluid flow rate and duration of operation can be selected within prescribed ranges in accordance with such factors as the nature and quantity of waste to be treated. Further parameters which affect waste processing include the dimensions of the conduits through which processed material and fluid flow. Preferably, the foregoing variables and parameters are selected to provide for the production of processed waste solids of a size in the range of from about 1/16 in. (1.5 mm) to about 1/4 in. (6.5 mm) in their largest dimension. A printout of system operation parameters such as waste temperature throughout the processing procedure can optionally be provided to render a permanent record of system operation. Alternatively, or in conjunction with printer operation, the various above-referenced operation various parameters can be stored in electronic memory for subsequent recall and display on a visually perceptible device such as a cathode ray tube (CRT) or similar display of alphanumeric and graphic data. In all instances, however, waste processing proceeds for a period of time which provides for grinding and exposure of the waste to a circulating stream of superheated water for a period of time that meets or exceeds the applicable standards and regulations governing material disinfection and sterilization in accordance with the selected form of waste treatment.

In a further aspect of the invention, methods and apparatus are provided for processing relatively large quantities of waste material, of on the order of several hundred pounds or more per hour, as is required for institutional facilities such as hospitals, laboratories, large restaurants, and other institutions. Institutional waste can be economically and efficiently processed on-site at such facilities in a manner that takes maximum advantage of existing facilities such as high pressure steam and/or hot water supplies. For example, institutions such as hospitals frequently have on-site high-pressure steam apparatus of on the order of 125 psi (325° F.) and/or hot water from boilers and the like which can be utilized to facilitate waste processing in accordance with the teachings of the present invention.

The methods and apparatus of the present invention that are especially applicable for industrial waste processing include a shredder hopper that is dimensioned to receive relatively bulky items of waste. Such waste can include aggregate medical waste that has been collected into color-coded bags designating special processing requirements, bulk linens that have been contaminated by various body fluids, mattresses and the like which would otherwise require disposal by conventional (i.e., incineration or burial) means. The hopper is operable to receive the waste and to direct it to a shredder assembly for preliminary volume reduction treatment by shredding. Shredded waste is directed to a high-capacity decontamination chamber, where the shredded waste is mixed with a suitable processing fluid such as water or an oil such as a vegetable oil like corn oil, mineral oil or a halogenated mineral oil for processing. The shredder hopper and shredder assembly are periodically cleansed and disinfected by application of a suitable disinfectant. Sensors within the decontamination chamber are operable to monitor volume level within the decontamination chamber in order to regulate in influx of waste material from the shredder and processing fluid from an appropriate fluid supply. Once a prescribed volume of waste has been received within the decontamination chamber, the delivery of shredded waste to the decontamination chamber is terminated, and the waste inlet to the decontamination chamber is sealed. The waste and fluid mixture is heated within the decontamination chamber and directed to a high-capacity chopper/pump, which grinds the waste to further reduce its volume and returns the fluid and entrained ground waste to the decontamination chamber for continued heating. The fluid and entrained waste is continuously processed and circulated by the chopper/pump and heated to the requisite processing temperature within a closed loop that extends from the decontamination chamber to the chopper/pump and back to the decontamination chamber for a prescribed time interval to ensure processing to a desired level of biological neutralization, as is the case with other embodiments of the present invention described previously.

Operation of the system is preferably monitored by various sensors having a suitable output to appropriate control apparatus to ensure processing of the waste in a thil-safe rammer. A record can optionally be rendered which details operation of the system as a function of time and temperature. Processed waste can optionally be filtered to separate solids in excess of prescribed dimension to permit for drying of the solids by suitable dehydration apparatus. Processed waste solids can optionally be compacted by suitable compacting apparatus to further reduce waste volume. The mixture of processing fluid and liquid waste can be cooled to a temperature within municipal requirements and passed into a sanitary sewer for disposal. In a further aspect of the invention, a portion of the processing fluid and liquid waste is collected following processing and returned to the decontamination chamber prior to cooling for use in processing of another waste processing cycle, thereby further reducing waste production and energy requirements for the waste processing system.

BRIEF DESCRIPTION OF THE DRAWINGS

The various objects and advantages of the subject invention will become more apparent from a reading of the following drawing figures, in which:

FIG. 4 is a top view of the waste decontamination chamber cover;

FIG. 5 is a side view of the cover and related cover locking hardware;

FIG. 6 is a frontal view of a waste control gate that can be positioned adjacent to the waste decontamination chamber outlet;

DETAILED DESCRIPTION OF THE PREFERRED EMBODIMENTS

Figure 1:
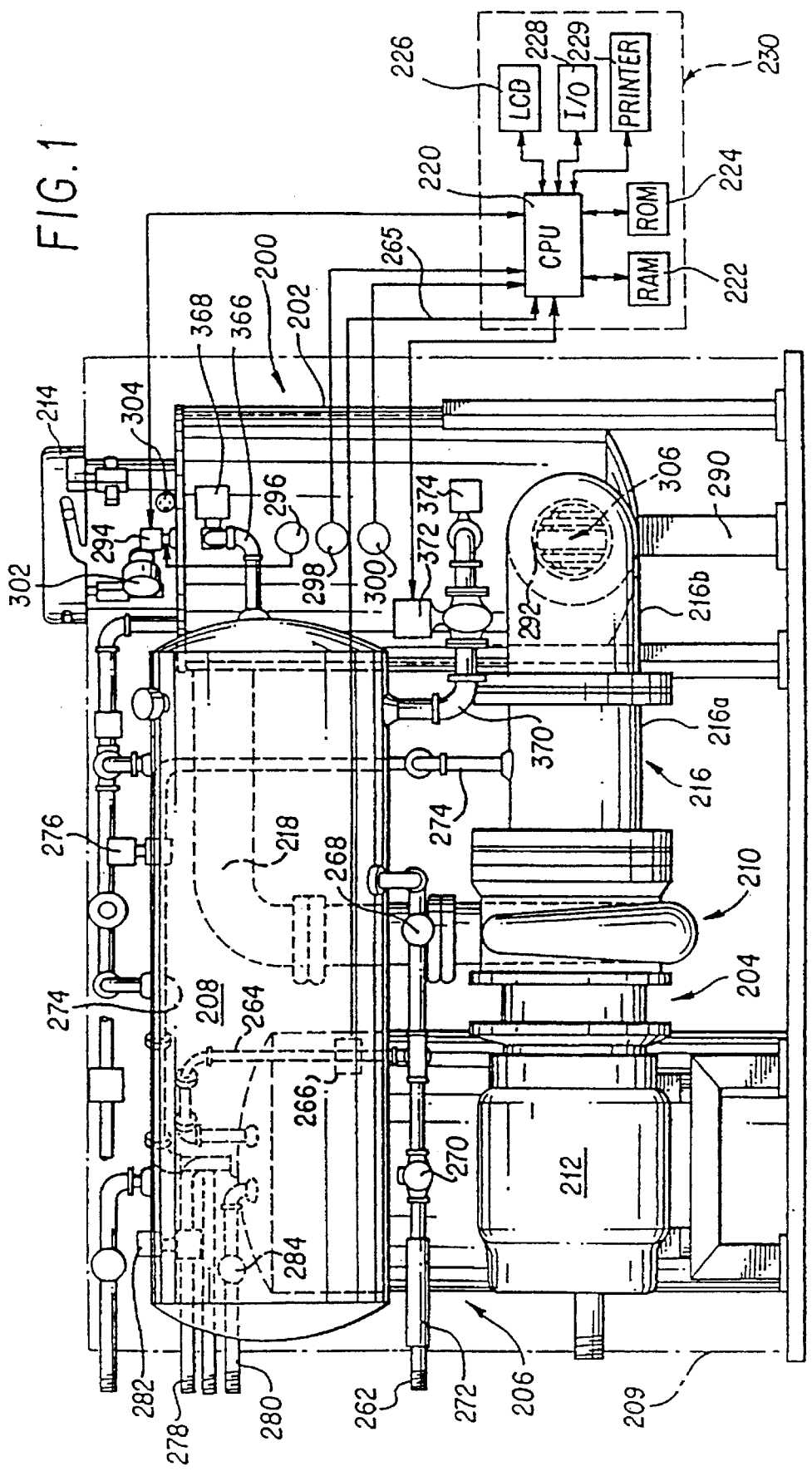
FIG. 1 is a side view of a waste processing apparatus in accordance with the present invention.
Figure 2:
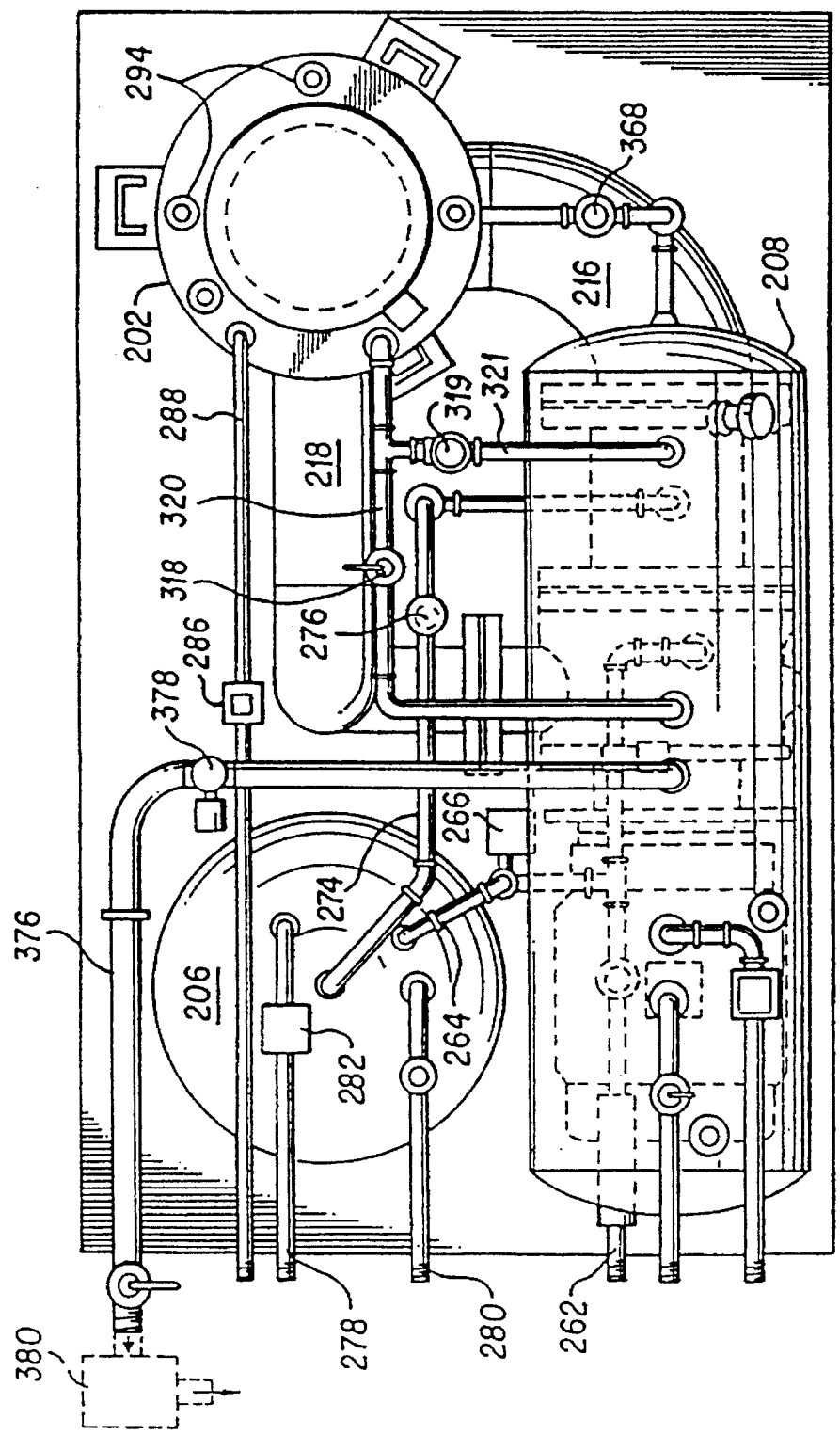
FIG. 2 is a top view of the apparatus depicted in FIG. 1.
Figure 3:
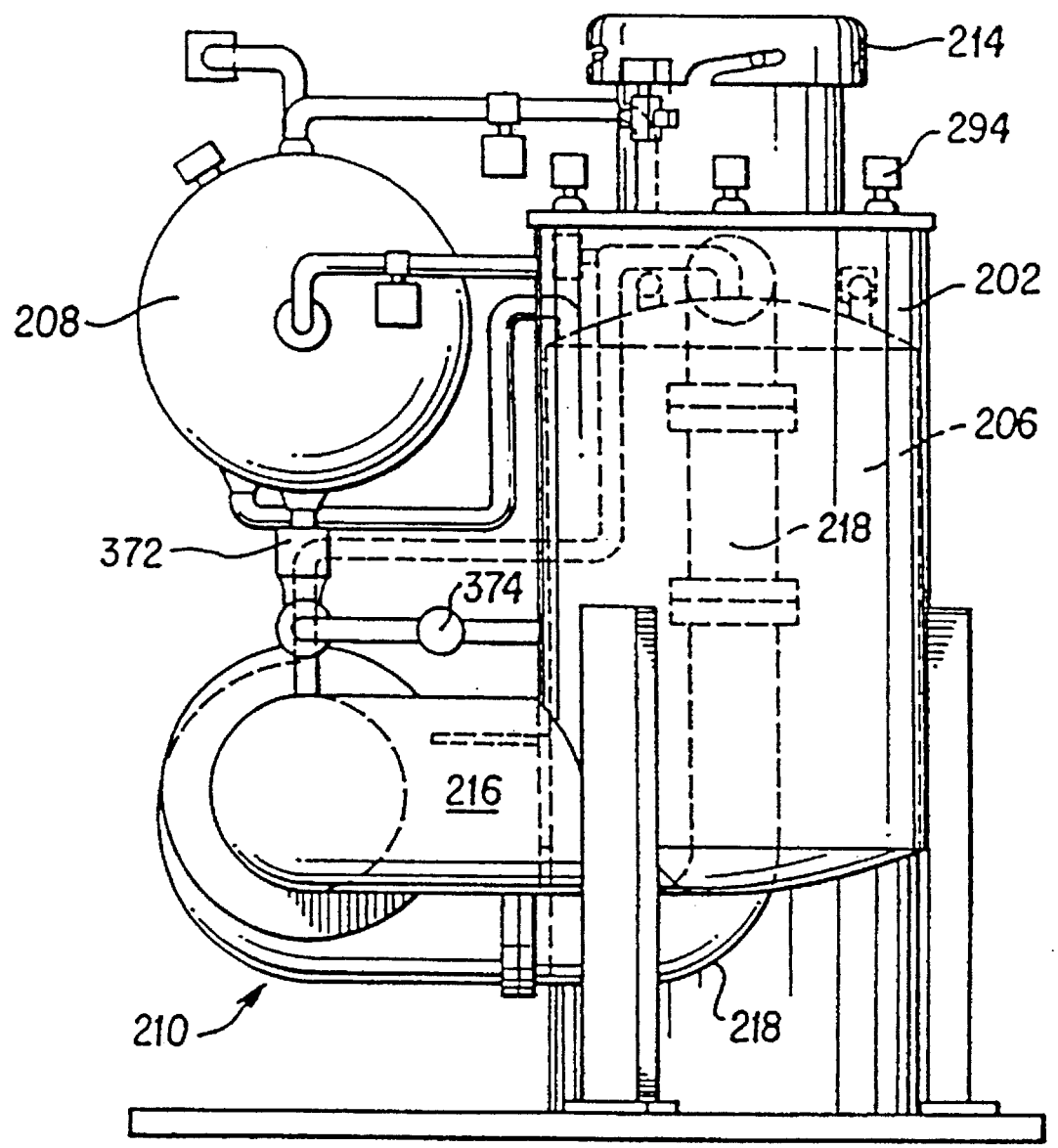
FIG. 3 is an end view of the apparatus depicted in FIG. 1.

With reference to the drawings, in which like reference characters represent corresponding parts throughout the various views, and with particular reference to FIGS. 1 through 3, there is depicted a waste processing system in accordance with the teachings of the present invention, designated generally by reference character 200. The system 200 is comprised generally of a decontamination chamber 202, a waste processing chopper/pump assembly 204 ("chopper pump"), a fluid reservoir 206 for heating and storing a fluid such as water to be mixed with the waste to be processed and a cooling tank 208 for receiving waste processed by the system and for cooling it prior to disposal. A housing 209 can optionally be provided to enclose the system and provide acoustic dampening. The chopper/pump 204 is generally comprised of a grinder assembly 210 and a motor assembly 212 for providing power to the grinder assembly. A removable cover 214 is provided over an inlet of the decontamination chamber 202 to permit user access to the interior of the chamber for depositing waste to be treated by the processing system 200. The waste can be in the form of virtually any type of non-toxic inorganic or organic material, such as medical waste, food waste, rubber, plastics, and the like for which it is desirable to disinfect, or optimally render biologically neutral (i.e., biologically inert or devoid of living organisms) via sterilization. Medical waste can include, by way of non-limiting example, sharps such as needles, knives and blades, trocars, clamps, glass containers, gauze and bandages, surgical gloves and gowns, and various other instruments and paraphernalia which contacts internal body fluids such as blood, lymphatic, semen and vaginal fluids. Waste sterilization is preferred in instances such as with some forms of medical waste where bacteria, viruses and/or spores may be present, in which case all living organisms associated with the waste must be destroyed prior to its disposal.

The invention is particularly useful for effecting sterilization of virtually all forms of non-toxic waste by exposing the waste to superheated water at a temperature in the vicinity of from about 270° F. (132° C.) to about 275° F. (135° C.) at a pressure of from about 55 psi to about 65 psi, thereby assuring that the fluid is maintained substantially in a liquid state. Waste treatment with superheated liquid water as opposed to water vapor is preferred due to its greater ability to intermix with the waste solids as they are ground and circulated by the chopper/pump 204. As will be described in considerably greater detail below, waste processing is accomplished by way of a closed, pressurized circuit which includes the decontamination chamber 202, pump 204, chopper/pump inlet conduit 216, grinder assembly 210, and the pump outlet conduit 218 extending between the pump 204 and the decontamination chamber 202. Accordingly, each of the circuit components is formed from suitable materials that are capable of withstanding the extremes of temperature, pressure and abrasion that are associated with operation of the waste processing system of the present invention.

The various aspects of system operation (i.e., temperature, pressure, material flow control and the like) are controlled by a control processor (CPU) 220. A random access memory (RAM) 222 is electrically connected to the CPU 220 and stores OSS (Operation System Software) software and provides working memory to the CPU. A read-only memory (ROM) 224 is also provided which stores various programs that are needed for input/output, power-up, self-test diagnostics, and the like for the CPU. A display 226 such as a liquid crystal (LCD), light emitting diode (LED) or cathode ray tube (CRT) display that is operable to provide human intelligible signal output to a system operator can optionally be provided. Various input/output (I/O) means 228 such as keyboards, switches and the like are preferably provided to permit user input to the CPU. A printer 229 can optionally be connected to the CPU 220 to provide a printout of various data associated with operation of the waste processing system 200. All of the foregoing electronic components (CPU, I/O and the like) are preferably provided at a system control panel 230 that is readily accessible to the system user.

Waste material to be processed by the system is deposited in the decontamination chamber through the chamber inlet 215 (FIG. 5). As the waste material and water is to be exposed to relatively high pressure, the cover 214 is configured so as to withstand these pressures and to prevent inadvertent opening during the course of system operation. Details of the cover construction are depicted in FIGS. 4 and 5. An oversized handle 232 is provided which extends across the cover to facilitate user manipulation of the cover to attain the requisite level of decontamination chamber sealing. A slot 234 is provided at four equidistantly-spaced positions along the side 235 of the cover. Each slot 234 extends away from a slot opening 236 at the rim 238 of the cover in a direction that is counter to the direction of cover rotation to effect seating of the decontamination chamber 202. The slots 234 are dimensioned to receive therein a corresponding key 240 which extends radically outwardly from the decontamination chamber outer surface adjacent to its inlet 215. Due to the rearward inclination of the slot 234, as the cover is rotated clockwise (i.e., toward a locked position in the depicted embodiment), each slot follows its correspondingly-received key 240, resulting in a downward exertion of pressure by the key 240 against the lower surface 242 of its corresponding slot.

A sensor 244 (FIG. 5) is provided along the chamber exterior adjacent to one of the keys 240. The sensor includes a plunger 246 that is reciprocally extensible with respect to a sensor housing 248. Biasing means such as a spring (not shown) received within the sensor housing 248 biases the plunger 246 (FIG. 5) outward from the housing 248 and into engagement with the cover rim 238. As the cover is rotatably advanced toward a closed position, the sensor plunger 246 is advanced into the housing 248 until it reaches a point within the housing that is commensurate with complete cover closure, at witch point an electrical signal is en-fitted from the sensor 244 to the control processor 220. Upon receipt of the sensor signal, the processor 220 transmits a signal to a solenoid 250 near the chamber inlet 215 to effect extension of a latch 252 from the solenoid housing 254 and into a correspondingly-dimensioned recess 256 formed in a latch receptacle 258 mounted to the exterior surface of the side 235 of the cover. Extension of the latch into the latch receptacle 258 is required before processing of waste material can proceed so as to ensure user safety from not only contamination with potentially infectious waste, but also from physical harm which could result from exposure to processed waste solids as they are returned under pressure to the decontamination chamber 202 following grinding. As a further precaution, the solenoid 250 is of the type which requires electrical signal input to effect either retraction or extension of the latch 252. Accordingly, the cover 214 is constructed so as to be incapable of being opened by ordinary means during the course of waste processing as well as in the event of a system or power failure during a material processing cycle, thereby ensuring that the cover is not opened until processing has been completed.

With reference once again to FIGS. 1 through 3, uncontaminated (i.e., fresh or non-potable) water is supplied to the reservoir or preheat tank 206 via supply line 262 for subsequent use in the sterilization process. Water is conveyed from the supply line 262 into the preheat tank 206 by an inlet pipe 264 when a control valve 266 such as a solenoid valve positioned in the inlet pipe 264 (FIG. 2) is biased in an "open" position. In an alternative embodiment, the preheat tank 206 can be incorporated into the decontamination chamber 202 in a manner that will be described in greater detail below, thereby dispensing with the cost and complexity of a separate preheat tank. In such instances, heating is accomplished by providing an array of band heaters. The valve 266, as is the case with all remotely controllable valves and pumps used in the system of the present invention, communicates in a conventional manner with the CPU 220 and receives operating instructions therefrom, as indicated by communication line 265 (FIG. 1), unless the specification explicitly or implicitly provides otherwise. Valve 266 is further operable to effect a pressure reduction in the incoming water stream from conventional inlet pressure (typically 60 psi) to about 8 psi. Another solenoid valve 268 is provided in the supply line 262 downstream from the pipe 264 to control water flow into the cool-down tank 208. The valves 266 and 268 are independently operable to provide for the control of fluid flow into their respective tank. A pressure relief valve 270 and fluid backflow preventer 272, as well as various other conventional plumbing apparatus that are conventionally used in fluid management, are also provided along the water supply line 262.

The preheat tank 206 is preferably in the form of a large capacity electric or gas-fueled water heater that is operable in a conventional manner, such as through the use of a thermostatically controlled burner or heater assembly, to maintain the stored water at an elevated, standby temperature of about 170° F. (77° C.) so as to expedite waste processing in the manner described below. A conduit 274 extends between the preheat tank 206 and the pump inlet conduit 216 to provide for the delivery of fluid from the preheat tank 206 to the flow of waste material en route to the pump grinder assembly 210 when the system 200 is in operation. Water flow through the conduit 274 is controlled by a solenoid valve 276 in accordance with CPU 220 signal output in the manner described above. A pair of ventilation outlets 278 and 280 extend from the upper end of the preheat tank 206. A solenoid valve 282 is positioned in the outlet 278 to provide for controlled venting of pressure within the preheat tank 206, whereas ventilation outlet 280 is provided with a mechanical pressure-responsive relief valve 284 that is operable in emergency situations to vent pressure from the tank 206 when the valve's trigger pressure has been attained. As the valve 284 does not communicate with the CPU 220, it is isolated from any problems that may arise with system electronics; instead, it is responsive solely to pressure exerted against it in its associated outlet 280.

The decontamination chamber 202 is configured as a pressurizable vessel that is capable of withstanding pressures in the range of from about 55 psi to about 65 psi. The chamber 202 can be formed from any suitable material that is capable of withstanding the extremes of temperature, pressure and abrasion that are associated with operation of the system. Suitable materials include, by way of example, stainless steel alloys and high impact, high temperature plastics. Prior to the commencement of waste processing, pressure within the decontamination chamber 202 can be equaled with atmospheric pressure to facilitate filling of the preheat and cool-down tanks 206 and 208. This can be accomplished by opening the normally closed solenoid control valve 286 in vent pipe 288 that extends from the decontamination chamber.

The decontamination chamber is oriented vertically as shown in the drawings to make use of gravity to assist in feeding of the waste to the pump assembly 204 and to minimize spatial demands. Tank support legs 290 can be provided to elevate the chamber above the ground and to position its outlet 292 at the lower end of the chamber at a level substantially even with that of the entrance to the pump inlet conduit 216.

With reference to FIGS. 1–3, a plurality of heaters 294 are provided at the upper end of the decontamination chamber 202 to provide for heating of the water from its elevated base temperature of about 170° F. (77° C.) as stored in the storage tank 206 to the optimal operating temperature of from about 270° F. (132° C.) to about 275° F. (135° C.) during the course of system operation in the manner set forth in detail below. The heaters are preferably in the form of electric resistance immersion heaters having a power output of about 5,000 watts each. However, the number and power output of the heaters 294 can be varied in accordance with such factors as the quantity and composition (i.e., solid, liquid, plastic, metal and so on) of the waste that is expected to be typically processed by a system user, as well as the rate of processing (i.e., system throughput) that is required by the user. The temperature and pressure within the decontamination chamber is sensed by respective temperature and pressure sensors 296 and 298 (FIG. 1), the output of which is directed to the CPU 220, which is operable to adjust various system operation parameters in the manner described below in instances where signal output from one or both of the sensors 296 and 298 is indicative of a measured value outside of a range of prescribed system limits. A further pressure sensor, designated by reference character 300, is provided with the decontamination chamber 202 to provide for deactivation of the fluid heaters 294 in the event that sensed pressure within the chamber exceeds a predetermined value. Output from the pressure sensor 300 is conveyed locally rather than through the CPU 220 to the heaters 294 in a manner known in the art (such as by way of circuit interruption to disable the supply of electric current to the heaters) to effect their deactivation. Fluid level sensors 302 and 304 are provided at the upper end of the decontamination chamber 202 to respectively monitor fluid levels within the chamber. Sensor 302 provides signal output to the control processor 220 to effect termination of the supply of water from the hot water tank 206 to the pump inlet conduit 216 when the decontamination chamber fluid level reaches a prescribed maximum. Sensor 304 is operable to provide signal output for deactivating the heaters 294 when the fluid level within the chamber 202 diminishes below a prescribed level.

As noted above, waste from the decontamination chamber 202 passes from the chamber outlet 292 to the chopper/pump assembly 204 through pump inlet conduit 216. In the depicted embodiment, the conduit 216 is comprised of two sections 216a and 216b to accommodate the lateral displacement of the pump assembly 204 relative to the decontamination chamber; however, a greater or lesser number of sections can be provided in accordance with the system design. A gate 306 (FIGS. 1 and 6) is provided at the decontamination chamber outlet 292, preferably at the interface between the chamber outlet and the pump inlet conduit 216, to control the passage of waste to the pump assembly. The gate 306 is preferably constructed so that all of its moving parts are maintained within the sterilization fluid flow in order to ensure complete sterilization of the gate during the course of waste processing. With reference to FIG. 6, the gate 306 is shown as being comprised of a generally annular gasket 308 that is formed from a high temperature resistant material such as a "Viton" elastomer. A plurality of apertures 310 are provided about the annular periphery of the gasket to receive therethrough appropriate fasteners such as bolts or rivets (not shown) that are used to secure the gate between the chamber outlet 292 and the waste conduit 216. A gasket tab 312 extends radially inwardly from a portion of the gasket 308 to which is secured in a conventional manner, as by rivets 314 or a suitable temperature resistant adhesive, a plurality of vertically arrayed bars 316. Because the gate bars 316 are secured to the tab 312 independently of one another, each is free to independently move to permit for the passage of waste material through the gate and to the chopper/pump assembly 204. The gate bars 316 can be provided with a generally flat or curved surface contour in their downstream (i.e., facing the viewer) direction in accordance with user preference to facilitate receipt within the curved interior of the pump inlet 216. The bars are formed from a temperature resistant, hardened material such as stainless steel or any other suitably hard and temperature and abrasion resistant material and are spaced up to several mm apart from one another to restrict passage of waste solids of a size in excess of the bar separation distance from passing through the gate to the pump assembly until the combination of fluid pressure upstream of the gate 306 (i.e., within the decontamination chamber 202) and vacuum pressure developed by operation of the chopper/pump assembly 204 as described below overcomes the inertia provided by the gate.

The chopper/pump assembly 204 can be of any suitable design which provides the requisite degree of waste material processing (i.e., grinding and chopping) and flow to accomplish the desired objective of processing of waste into relatively small fragments, thereby increasing its surface area for contact with high temperature water for effecting disinfection and optimally sterilization. In preferred aspects of system operation, the chopper/pump 204 is operable to process solid waste to a size in the range of from about 1/16 in. (1.5 mm) to about 1/4 in. (6.5 mm) to not only facilitate its exposure to the heated fluid, but also to reduce waste volume. The family of horizontal end-suction chopper pumps manufactured by the Vaughan Co., Inc. of Montesano, Wash., such as the model VP3E pedestal pump, are particularly applicable for use in the present invention. Use of this family of pumps is advantageous, because their respective motors 212 are oil cooled and lubricated, thereby ensuring that waste-contaminated water is confined to the prescribed waste and fluid circulation path. However, other motors which provide suitable amounts of torque, power, and confinement of the circulated fluid can be used.

Figure 7:
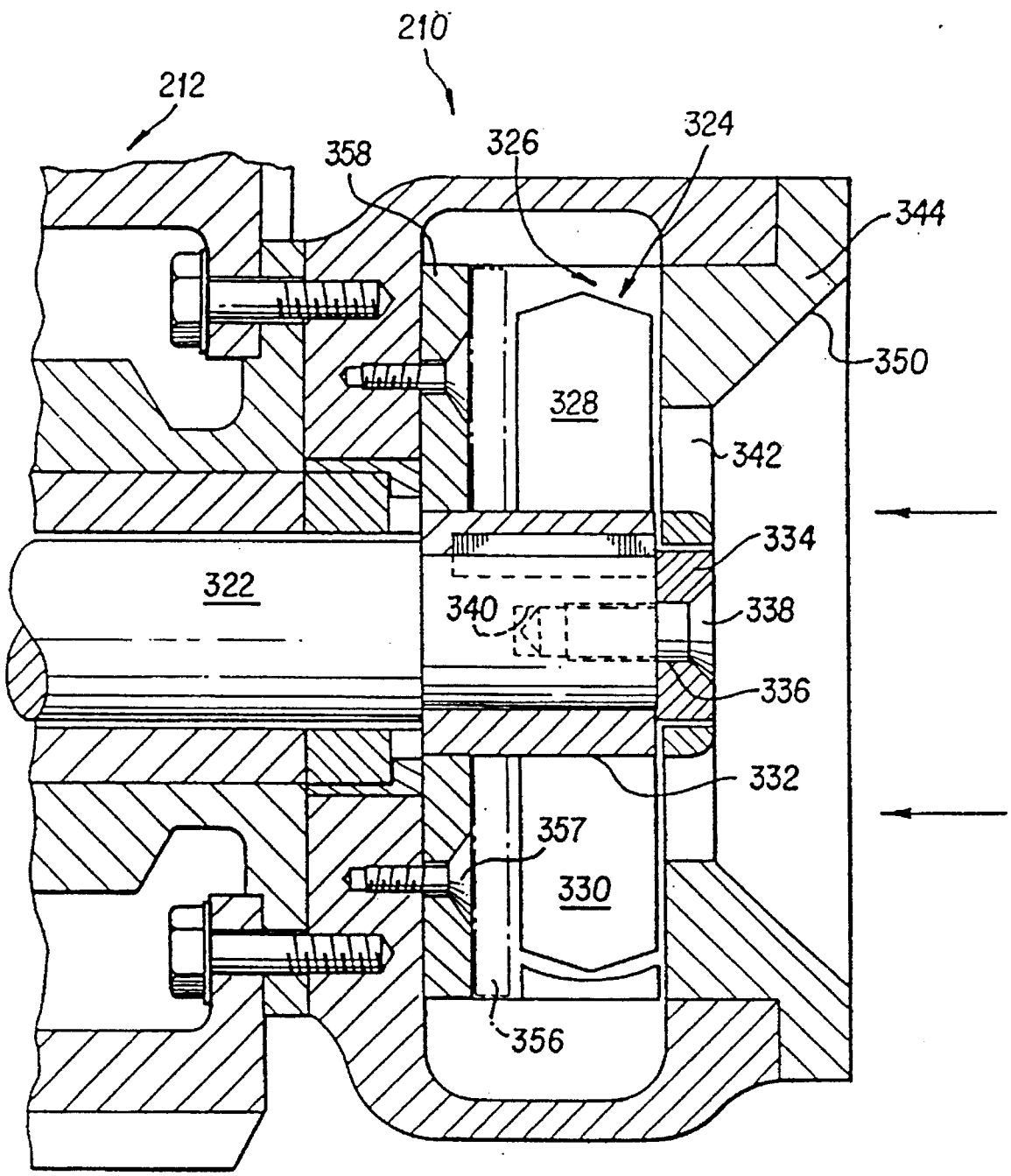
FIG. 7 is a sectional side view of a portion of the system pump assembly.
Figure 8A:
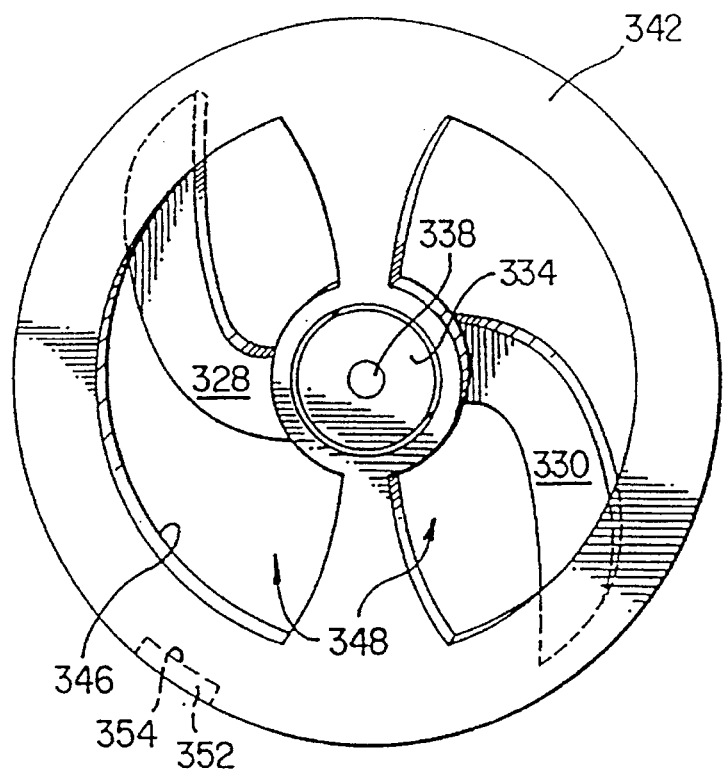
FIG. 8A is a frontal view of a portion of the system pump assembly.
Figure 8B:
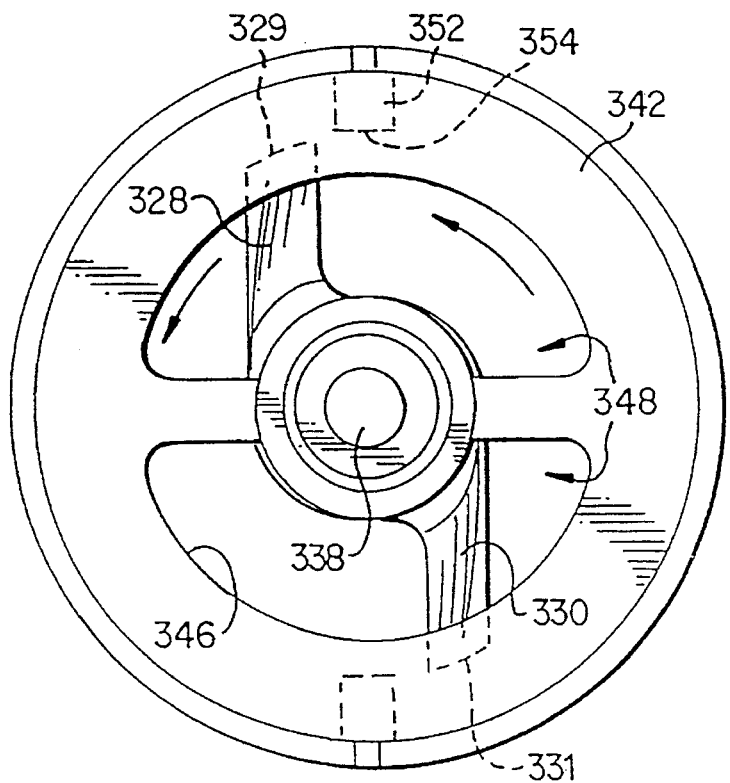
FIG. 8B is a frontal view of a portion of the system pump assembly.

With particular reference to FIGS. 7 through 8B, further details of the grinder and motor assemblies 210 and 212 are provided. The motor output shaft 322 extends into the grinder assembly 210 to provide rotational driving input (through an appropriate gear reduction assembly (not shown)) to an impeller 324 that is rotatably received within a venturi-shaped materials processing chamber 326. The impeller 324 includes a blade assembly that is comprised of a pair of generally opposed, curvilinear cutter blades 328 and 330 (FIG. 8A) that extend from a hub 332. The hub is fixedly secured to the free end of the motor output shaft 322 by a retaining plate 334 having an aperture 336 through which extends a conventional fastener, such as the depicted threaded fastener 338. The fastener 338 is received within a complementary-threaded and dimensioned recess 340 formed in the motor shall 322.

Positioned upstream (i.e., to the right side in FIG. 7) of the cutter blades 328 and 330 is a cutter plate 342 that is fixedly positioned with respect to the surrounding grinder housing 344. Alternatively, the cutter plate and grinder housing can be configured as a one piece, integral unit. The lower surface 346 of the cutter plate is provided with a hardened sharpened surface that is positioned in close proximity to the rotatably driven cutter blades 328 and 330 to provide for a compound cutting action of waste material that is interposed between the blades and the cutter plate surface. The cutting plate 342 defines a pair of laterally spaced elongated passages or apertures 348 through which waste material passes for cutting by the cutting blades 328 and 330. The housing 344 defines a wall 350 along its radial surface which extends radially outwardly in the upstream direction so as to guide waste material and fluid to the cutter blades. Cutting efficiency can be further enhanced by the provision of one or more cutter blocks 352 (FIGS. 8A and 8B) along a portion of the itmer periphery of the materials processing chamber 326. The radial inner edge 354 of each cutter block is provided with a sharpened surface which, together with the fixed cutting edge 346 of the plate 342, provides for enhanced cutting efficiency, as waste material is engaged, cut, and hurled forcefully there against by the rotatably driven cutter blades 328 and 330. Configuration of the blades 328 and 330 as generally opposed, nearly-extending members that are positioned on opposite sides of the hub 332 (FIG. 8B) can further enhance cutting efficiency. The distal ends 329 and 331 of the blades 328 and 330, respectively, are angularly inclined such that the forward, leading edge (in the direction of blade rotation, as indicated by the directional arrows) of each blade is provided with a length transverse to an axis from which it extends that is less than that for the trailing edge. This arrangement facilitates shearing action between the blade ends 329 & 331 and the curer blocks 352.

Cutting efficiency can be further augmented by the provision of an auxiliary cutting plate 356 (depicted in phantom in FIG. 7) downstream of the cutter blades which can be provided with any of a variety of suitable configurations which supplements the cutting effectiveness of the rotatably driven blades 328 and 330. The auxiliary plate can be fixedly secured by threaded fasteners 357 or other suitable fastening means to the base 358 of the materials processing chamber 324 as shown, or can be elevated and supported therefrom by appropriately dimensioned spacers (not shown) in instances where the auxiliary cutting plate is provided with cutting passages of the type described above with reference to cutting plate 342. In one aspect of the invention, the motor is operable to rotate the blades 328 and 330 at a variety of different speeds (typically in the range of from about 1700 rpm to about 1900 rpm) in accordance with the waste composition (i.e., liquids, textiles, metals and so on) and such user-selectable parameters as flow rate through the system. Alternatively, a single motor speed can be provided for processing the waste without regard to its composition. Waste processing in both schemes of operation is to continue for so long as necessary to ensure that the waste is exposed to superheated water (i.e., temperature exceeding 270° F. (132° C.)) for a minimum of six minutes or longer in instances where waste sterilization is to be effected. as will be described in greater detail below. Because a variety of different types of waste are capable of being handled by the waste processing system of the present invention, all cutting surfaces are formed from suitably durable materials, such as hardened metal alloys and/or metals provided with a suitable chemical coating in a rammer well known in the field of metallurgy.

With reference again to FIGS. 1 through 3, ground waste material and fluid processed by the grinder assembly 210 is urged through the materials processing chamber to the decontamination chamber 202 through grinder outlet 218, thereby providing a closed system for continued waste processing in the mariner to be described below. During the course of system operation, the fluid heaters 294 are activated to elevate the temperature of the water and entrained waste material to the desired operation temperature (to effect sterilization) and the pump 204 is operated for a period in excess of the requisite period of time that is accepted for effecting the desired disinfection or sterilization (in accordance with user instructions) in order to ensure sterilization of not only the waste material and fluid, but all of the waste processing hardware with which the waste and fluid comes into physical contact. The closed fluid path is maintained at a pressure of from about 55 psi to about 65 psi to ensure that the water introduced into the system for effecting sterilization maintains substantially a liquid state of matter. As mentioned above, sterilization with liquid water rather than water vapor is preferred to ensure full contact and penetration (where applicable) of waste solids to effect sterilization of even compact, porous materials such as textiles and gauze which can readily absorb potentially infectious bodily fluids. Excess pressure can be vented from this closed system into the cool-down tank through the operation of valves 318 and 319 (FIG. 2). Valve 318 is positioned in vent pipe 320 which extends between the decontamination chamber 202 and the cool-down tank 208 and is in the form of a self-actuating pressure relief valve that is operable to open and permit communication between the chamber 202 and tank 208 once its set pressure has been attained. Valve 319, which is positioned in line 321 which branches from pipe 220 to the cool-down tank, is a solenoid valve under the control of the CPU 220 and is operable during the waste material cool-down cycle described below to release pressure from the decontamination chamber 202.

Once the prescribed period for waste sterilization in the system has passed, the sterilized liquid and entrained waste solids (collectively referred to as "waste mixture") are directed to the cool down tank 208 from the decontamination chamber 202 through inlet pipe 366. Flow into the inlet pipe 366 is controlled by solenoid valve 368, which is ordinarily biased in a closed position to prevent premature cooling of the waste material prior to completion of the required disinfection or sterilization cycle. As the waste mixture is received within the cool down tank 208, cool water contained within the tank 208 is admitted into the decontamination chamber 202 along conduit 370 (FIG. 1). A fluid pump 372 is provided in the conduit 370 to supply a pressurized flow of cooling water to the decontamination chamber. A valve 374 such as a ball valve is provided in the conduit to ensure unidirectional fluid flow into the decontamination chamber once the pump 372 has been activated. As the waste mixture is circulated by the pump assembly 204 throughout the closed system and cool down tank, the mixture is cooled from the temperature that was necessary to ensure the desired disinfection or sterilization to a temperature which satisfies any prevailing municipal requirements for waste disposal into, for example, a municipal sewer system. Once the temperature of the cooled waste mixture has diminished to the requisite disposal temperature, it is directed by the operation of pump 372 (FIG. 1) from the cool down tank, upon opening of solenoid valve 378, through a disposal conduit 376 (FIG. 2) for removal from the processing system. Preferably, the waste solids are separated from the liquid, as can be accomplished by filtration through filter assembly, depicted in phantom and denoted generally by reference character 380, prior to disposal, thereby reducing by several orders of magnitude the volume of waste solids to be disposed for many waste materials.

The principles of the invention may be applied to the treatment of waste coated plastic material, whereby treatment results in the removal of substantially all coating(s) from the surface of the coated plastic material. No changes whatever need be made to the system in order to achieve coating removal, as opposed to achieving biological neutralization. In operation, the waste to be processed is waste coated plastic material. Circulation within the closed waste processing circuit results in the removal of substantially all coating(s) from the surfaces of ground plastic solids. Processing temperatures for removing coating from plastic range from about 250° F. (121° C.) to about 450° F. (232° C.), preferably 275° F.–370° F. (135° C.–188° C.), which temperature depends in part upon the melting temperature of the plastic. For thermoplastic olefin, which has a melting temperature of 329° F. (165° C.), the processing temperature preferably is about 278° F. (137° C.) and circulation continues until about substantially all coating(s) from the surface of the coated plastic material is removed. The ground plastic solids then are filtered from the waste liquids, which liquids contain the removed coating(s).

The principles of the invention may be applied to the treatment of water soluble polymeric or fibrous waste materials, whereby treatment results in the dissolution of the waste material. The system can be used without any changes to achieve the dissolution of this waste material, as opposed to biological neutralization. In operation, the waste to be processed is water soluble polymeric or fibrous waste material. Circulation within the closed waste processing system results in the dissolution of the waste material. Processing temperatures for dissolving the water soluble polymeric or fibrous waste material range from about 175° F. (79° C.) to about 250° F. (121° C.), preferably about 185° F. (85° C.) to about 205° F. (96° C.). Since temperatures below the boiling point of water are preferably used, the treatment can be performed at lower pressure. Suitable pressure range from about 5 to about 25 psi, preferably from about 5 to about 15 psi. The circuit components of the system for this specific use are formed from suitable materials that are capable of withstanding the temperature, pressure and abrasion associated with the operation of the waste processing system for treating water soluble polymeric or fibrous waste material. Since lower temperatures and pressures are used in this embodiment as opposed to biological neutralization, different kinds of material, known to a skilled artisan, can be used for the circuit components than are used for biological neutralization. The treatment of the water soluble polymeric or fibrous waste material according to the present invention results in the dissolution of the material. The processed liquid can be discharged into, for example, a municipal sewer system.

SYSTEM OPERATION

Figure 9A:
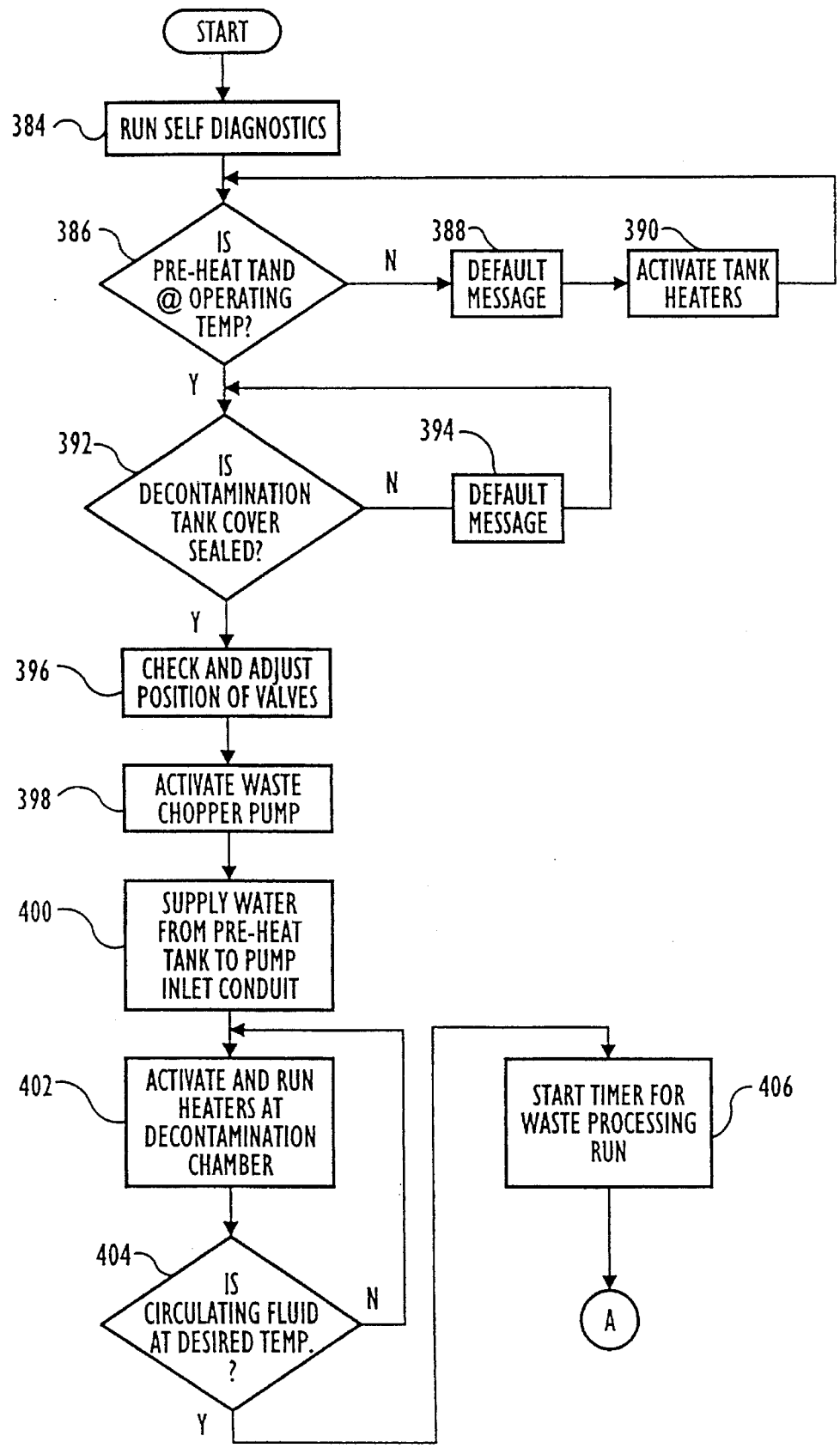
FIG. 9A is a flow diagram of the operational control arrangement for the present invention.
Figure 9B:
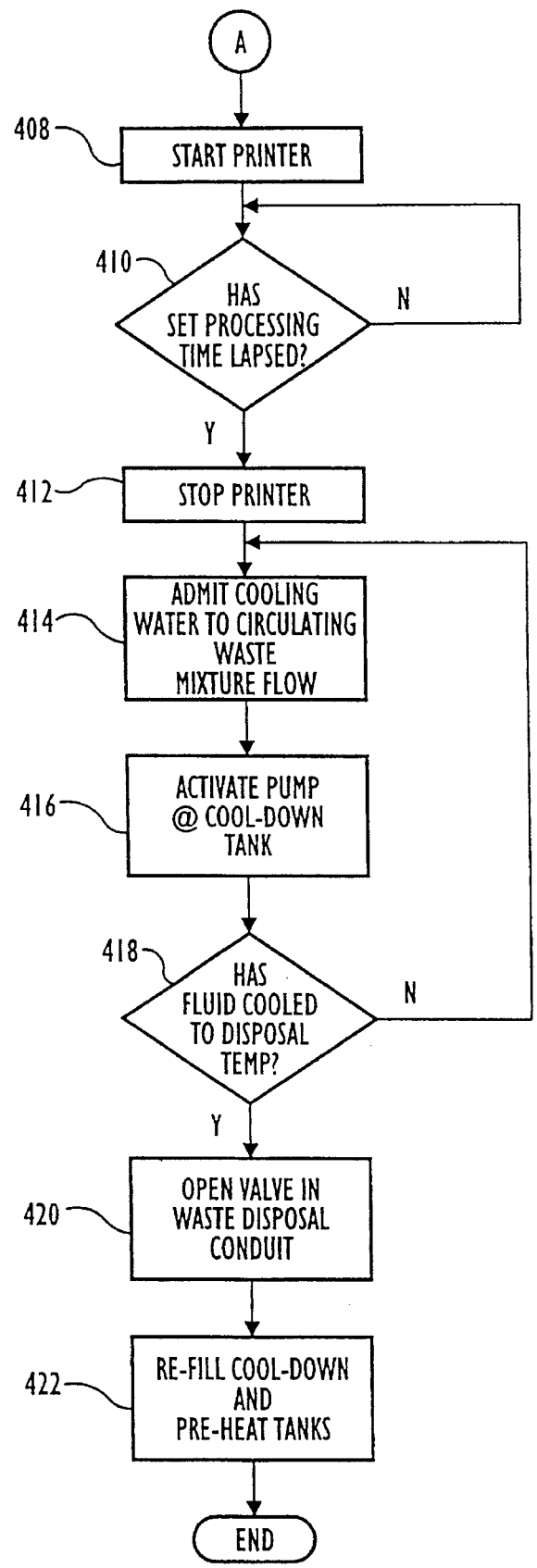
FIG. 9B is a flow diagram of the operational control arrangement for the present invention.

The operation of the waste processing system 200 of the present invention will now be described with reference to the flow diagram illustrated in FIGS. 9A and 9B, with concurrent reference to FIGS. 1 through 3.

Waste to be processed is deposited in the decontamination chamber 202 and the lid 214 therefor is closed and sealed. Prior to the commencement of waste processing, the CPU 220 is operable in accordance with program control from RAM to run a self-diagnostic check of the system electrical and electrically-operated components such as various valves and temperature and pressure sensors which communicate with the CPU, as indicated by block 384 in the flow chart. Communication between such electrically operable components and the CPU is indicated in FIG. 1 by a communication line extending between the controlled part and the CPU. An example of such a communication line is provided by line 265 which extends between valve 266 and the CPU 220. It is to be understood, however, that similar communication lines exist between the CPU 220 and each part with which the CPU communicates, either in a unidirectional or a bi-directional manner. For the sake of clarity, however, such lines have not been included in FIG. 1, but they are understood to be present in order to provide the requisite control for system operation as described previously and below.

Upon successful completion of the self-diagnostic test, the CPU 220 receives signal input from a temperature sensor included with the preheat tank 206 that provides an indication of the temperature of fluid within the tank, as indicated by decision block 386. In instances where fluid temperature is below prescribed system operating limits for the system 200, as may be the case when the tank has recently been replenished with tap water, a "default" message conveying to the system user the lack of readiness of the system to commence operation is produced in the display 226, as indicated by block 388, and the heating elements included with the tank are switched on to bring the fluid stored within the tank to operating temperature, noted by block 390.

In instances where the preheat tank fluid temperature meets the pre-established operating temperature, the CPU 220 is then commanded to analyze input from the decontamination chamber cover solenoid 254 (FIG. 5) to determine whether or not the cover 214 has been properly sealed, as shown by block 392. An appropriate default message such as "close cover" (block 394) is generated for display to the user via console display 226 in instances where output from the solenoid 254 to the CPU 220 along an appropriate communication line (not shown) is indicative of incomplete cover closure. If the output from the solenoid 254 is of a character that confirms cover closure and sealing, the CPU 220 is operable to communicate with the various valves and pumps under its control to confirm their respective proper orientation (i.e., "closed" or "open") prior to commencement of system waste handling (block 396) and to adjust the valves accordingly in instances where the valve position or pump operation status communicated to the CPU 220 does not comply with the system operating program stored in RAM 222.

Once the foregoing system operation statuses have been confirmed and corrected as required, the CPU 220 is operable to deliver signal input to the chopper/pump assembly 204 to effect chopper/pump operation at the prescribed rate of speed (block 398) and to deliver signal input to the valve 276 to permit a flow of heated fluid from the preheat tank 206 to the pump inlet conduit 216 (block 400). Fluid delivered from the tank 206 is conveyed by the chopper/pump 204 to the decontamination chamber 202 through pump outlet 218, where the fluid mixes with the waste material deposited therein. Once fluid pressure within the decontamination chamber 202, in combination with the negative pressure exerted by the chopper/pump 204, exceeds the inertia of the waste gate 306, waste solids pass with the fluid flow to the chopper/pump grinder assembly 210, where they are chopped and ground by the rotating cutter blades 328 and 330 and cooperating cutting surfaces of the cutter plate(s) 342 and 356, and conveyed into outlet 218 for recirculation to the decontamination chamber 202. Fluid level sensor 302 provides signal output to the CPU to convey the fill status of the decontamination chamber as water is delivered from the preheat tank into the circulating sireran of water and liquid and solid waste material in the manner described above.

As the fluid and waste mixture is circulated between the decontamination chamber and chopper/pump through the respective pump inlet and outlet conduits 216 and 218, the CPU 220 is operable to activate the decontamination chamber heaters 294 (block 402) to elevate the temperature of the circulating stream to the operating temperature that is required to effect the selected level of processing. In this regard, a temperature in the range of 270° F. (132° C.) is to be maintained for a continuous period of at least six minutes to effect waste sterilization, whereas a lesser temperature on the order of at least about 212° F. (100° C.) is preferred for disinfection. Temperature data from the decontamination chamber is conveyed by sensor 296 to the CPU, which continues signal output to the heaters 294 (block 404) until the fluid temperature as sensed by sensor 296 reaches the desired operating temperature. Once this temperature has been attained, a timer (not shown) such as that typically provided for CPU operation is started, as noted by block 406. Additionally, a printer, which can optimally be provided with the system to document such system parameters as fluid temperature, is also actuated (block 408).

As the waste processing cycle continues in the foregoing manner, the CPU is operable to compare clock and temperature sensor 296 output data with the preselected time and temperature parameters stored in CPU memory to allow for determination of whether the required time of material processing at the requisite temperature set forth in the CPU operating program has lapsed (block 410). This comparison process continues until the clock and temperature data provided to the CPU 220 indicate that the requisite period has passed, at which time the printer is deactivated (block 412) and the CPU is operable to effect cooling of the water and entrained waste solids and liquids ("waste mixture"), as indicated by block 414.

The CPU 220 implements cooling of the waste mixture by directing valve 374 in the cooling tank conduit 370 to open and pump 372 to commence pumping of cool (i.e., ambient temperature or chilled) water into the decontamination chamber 202, as indicated by block 416. The CPU 220 also commands valve 368 in inlet pipe 366 to open, thereby admitting a portion of the circulating waste mixture with the cool-down tank 208. The CPU monitors the temperature of the circulating waste mixture (block 418) and continues to supply cool water until the temperature diminishes to the desired level for disposal. The desired cooling temperature may, for example, be that temperature established by municipalities at which qualifying waste material can be passed into the sewer or other municipal disposal system. Once the temperature has reached the requisite cool-down temperature, the CPU 220 directs waste valve 378 in disposal conduit 376 to open (block 420), thereby allowing for the disposal of the cooled waste mixture from the cool-down tank 208. Waste solids in excess of a predetermined size can optionally be filtered from the waste mixture passing through the disposal conduit to pennit its disposal apart from the liquid component of the waste mixture. Such waste solids, by virtue of having been processed in the foregoing manner, can be disposed of in a conventional manner in a compact form, thereby lessening the burden on waste disposal facilities and on the waste originator in providing for safe and efficient waste disposal. The CPU is operable thereafter to provide for refilling of the respective preheat and cool-down tanks (Block 422) to replenish their supplies of water used in the foregoing processing cycle. Tank refilling is accomplished as a result of CPU 21 signal input to valves 266 and 268 directing their respective opening, thus allowing for replenishment of associated preheat tank 206 and cool-down tank 208 respectively, with fresh water for use in a subsequent waste processing cycle.

Figure 10:
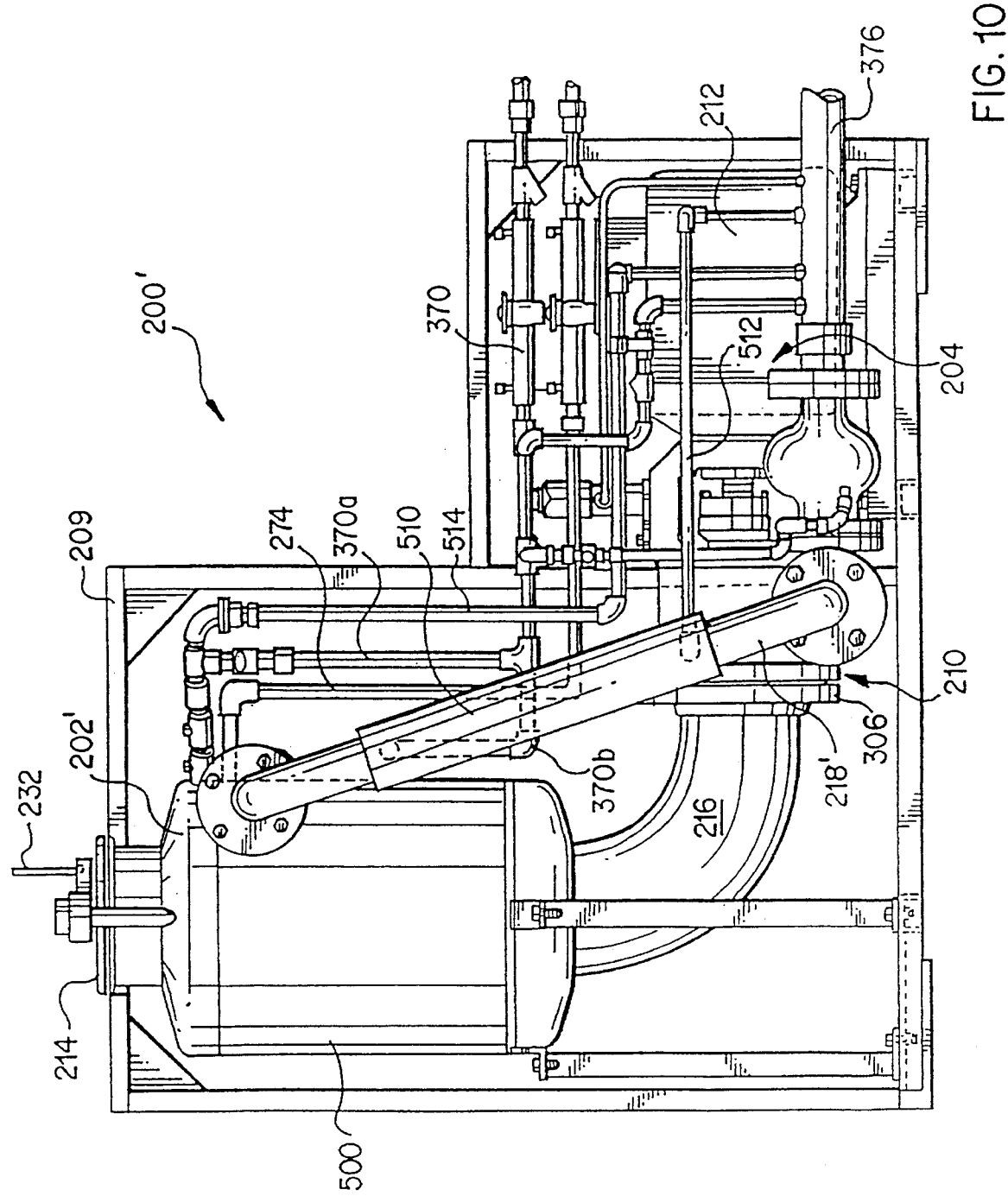
FIG. 10 is a sectional side view of an alternative configuration of a waste processing system in accordance with the present invention.

With reference to FIG. 10, there is depicted an alternative aspect, designated generally by reference numeral 200', of the waste processing system 200 described above. In this alternative embodiment, the waste processing system has been simplified to include three major components: a decontamination chamber 202', chopper/pump 204, and a return conduit/cooling unit 218'. This arrangement is advantageous for its simplicity, reduction in the number of components, spatial and power requirements, and cost of manufacture. Moreover, the illustrated embodiment can be configured as a pressurized or non-pressurized unit, in accordance with the type of processing fluid (i.e., aqueous or non-aqueous) that is to be employed. As has been discussed previously, water can be used as a processing fluid, in which instance the processing system must be provided with appropriate fittings, seals and componentry that is adapted to withstand the 55–65 psi range of pressures that are required to maintain the water at a superheated temperature of on the order of 270° F.–275° F. (132° C.–135° C). Alternatively, use of a non-aqueous fluid having a boiling point at atmospheric pressure that is in excess of 275° F. (135° C.), and preferably in excess of about 300° F. (149° C.), allows for operation of the system at or near atmospheric pressure, thereby providing for a commensurate reduction in the cost of system manufacture, as only high temperature, as opposed to high temperature and pressure, components can be used in fabrication of the waste processing system.

With continuing reference to FIG. 10, the decontamination chamber 202' includes a removable cover 214 that permits for selective access to the interior of the chamber 202' for the introduction of waste to be processed. A heating system 500, such as an array of band heaters or an insulated jacket that is operable to receive high temperature steam from a steam source, is mounted along at least a portion of the decontamination chamber in heat conductive relation therewith. The heating system is operable to heat the contents of the chamber to the aforementioned temperature range of 270° F.–275° F. (132° C.–135° C.) that is necessary to effect sterilization over the prescribed operation time interval of about six minutes. A processing fluid such as water or oil that has preferably been preheated to a temperature of at least 160° F. (71° C.) is admitted to the decontamination chamber through a supply line 274 in the manner described previously. Upon confirmation of cover closure in the manner described previously, the pump 204 is operable to draw waste from the decontamination chamber 202', through inlet conduit 216, to the grinder 210, which is operable to grind the incoming waste and return the ground waste to the decontamination chamber 202' through return conduit 218'. A closed, high temperature circuit is therefore established that extends from the decontamination chamber 202', to the inlet conduit 216, chopper/pump assembly 204, and return conduit 218'. This closed circuit is pressurized to between 55 psi and 65 psi in instances where aqueous processing fluids are employed, as has been discussed previously.

Processing fluid and entrained, ground waste material are continuously circulated via operation of the chopper/pump 204 through the closed circuit for the prescribed time interval once the preestablished treatment temperature has been attained. The temperature of the circulating waste-fluid mixture is monitored, preferably continuously, to ensure attainment of the desired degree of biological neutralization. System control software is operable to activate the heating system to ensure that the temperature of the circulating mixture is maintained at the desired temperature level.

Upon completion of a treatment cycle, a flow of cooling fluid such as tap water is admitted into the processing circuit from a supply conduit 370. The cooling fluid is admitted via branch 370a to the processing circuit at the upper end of the decontamination chamber 202'. Cooling fluid is also supplied via branch 370b to a cooling jacket 510 that surrounds the return conduit 218' to augment cooling of the processed fluid-waste mixture. The flow of cooling fluid is regulated by valves (not shown) that are associated with the supply conduit 370 and/or each of the supply branches. The cooling jacket can be provided with an appropriate integral configuration to increase the surface area for heat exchange with the exterior surface of the enclosed return conduit 218'. Cooling fluid admitted to the cooling jacket 510 passes there from via outlet conduit 512. Once the processed fluid-waste mixture has been cooled to a prescribed temperature, valves (not shown) associated with waste discharge line 514 open to permit the passage of the fluid-waste mixture from the decontamination chamber into the disposal conduit 376 for removal from the system.

The fluid-waste mixture that is directed into disposal conduit 376 is passed through a filter to separate waste solids of a prescribed minimum dimension from the remaining waste solids and fluid mixture. The separated waste solids can be further processed by drying and/or compacting to further reduce their volume prior to disposal. Additionally, at least a portion of the fluid can be recovered and ultimately returned to the decontamination chamber 202' for use in a subsequent waste processing cycle. Such recovery can be advantageous in instances where the processing fluid is an oil, for which discharge into a sanitary sewer is not desirable or permissible, as well as in instances where it is desirable to utilize the residual heat stored in the processed fluid, thereby saving energy requirements for subsequent processing cycles.

Figure 11:
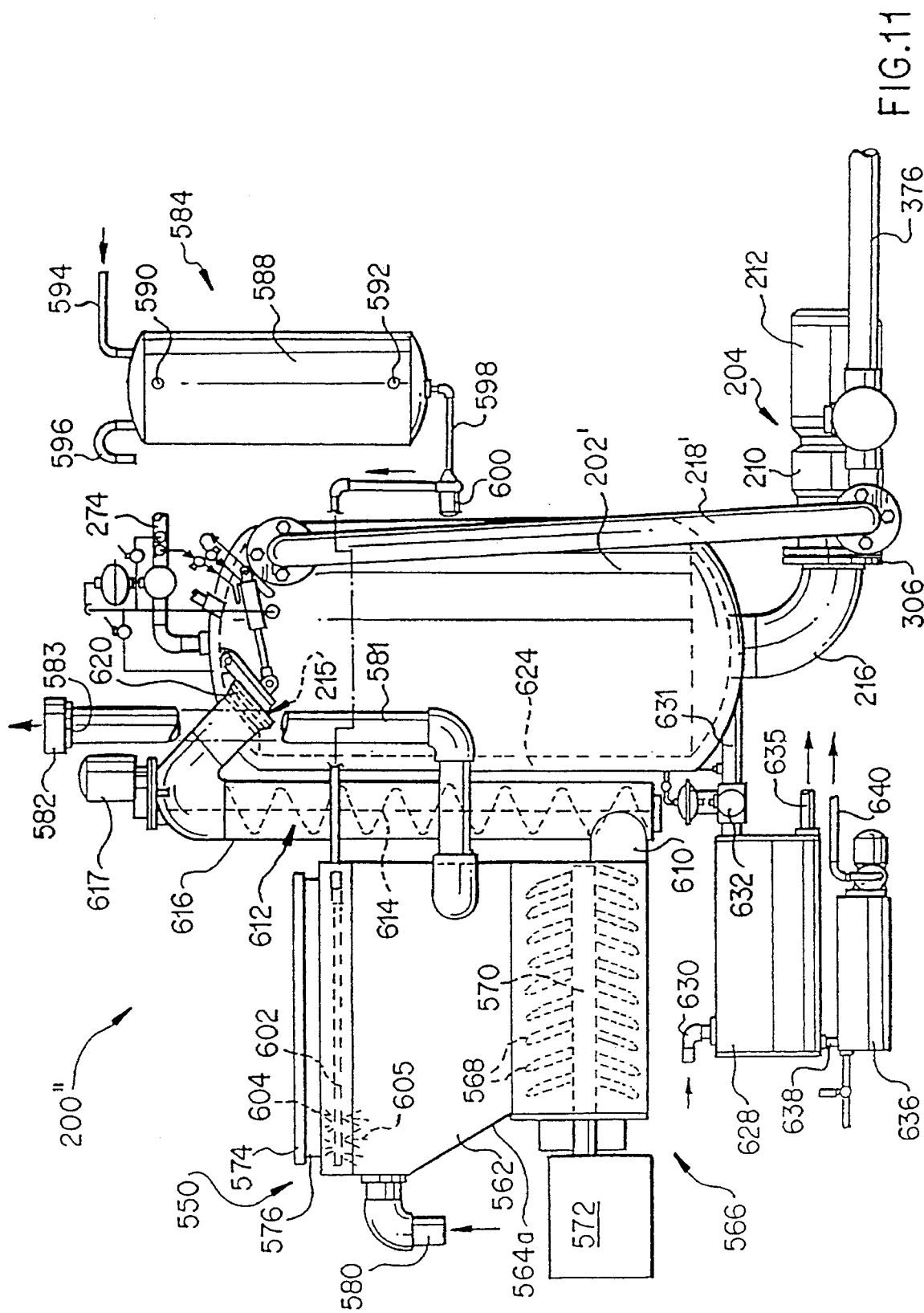
FIG. 11 is a sectional side view of a further alternative configuration of a waste processing system in accordance with the present invention that is particularly adapted for processing bulk waste material.

In a further alternative embodiment of the present invention, depicted in FIG. 11, a waste processing system 200" is provided that is operable to process bulk waste, such as aggregate medical waste that has been collected in appropriately-designated bags, linens and gowns, mattresses and the like. General operating principles of the depicted waste processing system 200" are similar to those that have been described in connection with the processing system 200' depicted in FIG. 10. In particular, the processing system includes a decontamination chamber 202' that is operable to receive and to heat (via associated heating apparatus 500 discussed previously) waste material and a processing fluid such as water, as well as an oil such as vegetable oil, mineral oil and the like that have boiling points in excess of 270° F. (132° C.) to about 275° F. (135° C.), and preferably in excess of 300° F. (149° C.). A waste conduit 216 extends from the decontamination chamber 202' to deliver waste material to a chopper/pump assembly 204, which is operable to chop solid waste material, mix the ground material with the processing fluid and direct the processing fluid and entrained ground solids to the decontamination chamber 202' so as to circulate the waste material in a closed processing circuit in the n-trainer described previously. The components of the waste processing system 200" are of a larger scale than are those for any of the foregoing processing systems in view of the volume. As has been discussed previously, the processing circuit is configured as a pressurized or non-pressurized circuit in accordance with the type of processing fluid (aqueous or non-aqueous) in use.

Waste material of the foregoing variety is supplied to the decontamination chamber 202' by means of a shredder assembly, which is designated generally by reference numeral 550 in the drawing figure. The shredder assembly includes a hopper 562 that is provided with a plurality of sidewalls 564, at least one of which (564a) is preferably angularly inclined to direct waste received within the hopper toward a shredder unit 566. The shredder unit includes an array of tines or blades 568, depicted schematically in the drawing, that are mounted to a shaft 570 rotatably coupled to a motor 572. Rotation of the shaft directs the tines into engagement with the waste 24 material to tear and shred the waste material prior to its receipt within the decontamination chamber 202' in the mariner to be described below.

Access to the interior of the shredder hopper 562 is controlled by a cover 574 that is displaceably mounted to the hopper by an appropriate set of hinges 576. The disclosed waste processing system 200" may be automatically supplied with waste for the hopper 562 by way of a variety of conventional supply systems, such as conveyor belts and roller assemblies (not shown). Alternatively, waste can be manually supplied to the hopper, in which case it is desirable to ensure that the shredder assembly and waste inlet passage to the decontamination chamber 202' is maintained under negative pressure to ensure thin waste material and contaminants entrained in the waste material are not free to escape from the hopper 562 during its supply with waste material or its operation. Such operational constraints are especially important in instances where biological and/or medical waste are to be processed, in which case it is desirable to control the spread of airborne pathogens, bacteria, viruses and the like. An air inlet conduit 580 extends from one of the hopper sidewalls to provide for the entry of atmospheric air into the hopper 562. Negative pressure is established within the shredder assembly by drawing air from the hopper through exhaust conduit 581 that extends away from the hopper. An exhaust fan 582 provides a source of negative pressure to draw the air from the shredder assembly 550. Prior to discharge from the conduit 581, the evacuated air is passed through a HEPA filter 583 to remove contaminants from the air flow in excess of a prescribed size. Provision of the foregoing air management system in the shredder assembly serves to restrict the flow of airborne contaminants from the hopper and minimize the risk of contamination of personnel working in the vicinity of the waste processing system.

As the interior of the shredder assembly 550 is not processed to a level of biological neutralization with the waste material received therein in the manner described in the previous embodiments (FIGS. 1–10), a cleansing system, denoted generally by reference numeral 584, is provided to effect periodic cleansing and disinfection/sterilization. The disinfection system includes a reservoir 588 for receiving a volume of a suitable fluid disinfecting agent. Fluid level sensors 590 and 592 are operable to provide appropriate signal output to control electronics 220–230 (FIG. 1) to indicate tank "full" and "low" level conditions, respectively. Disinfectant can be supplied from an appropriate source (not shown) to the reservoir 588 through an inlet 594 upon detection of a diminished fluid level within the reservoir. Vent 596 is provided to facilitate fluid 25 flow from the reservoir 588. Fluid flows from the reservoir and into fluid line 598 upon opening of pump/valve 600 to provide for delivery of disinfectant to a spray head 602 located within the hopper assembly 550. A plurality of apertures 604 are provided along the spray head 602 to permit for the release of disinfectant 605 in liquid or vapor form from the spray head. In a preferred aspect of the invention, operation of the pump/valve 600 is governed by the control electronics in accordance with appropriate program input to implement cleansing of the shredder assembly 550 in accordance with a prescribed schedule.

Waste processed by the shredder assembly 550 is directed under positive pressure through conduit 610 into a material advancement unit 612. The advancement unit 612 is provided in instances where spatial requirements for the waste processing system 200" are such that it is not possible to position the shredder assembly 550 with respect to the decontamination chamber inlet in a manner which permits for effective gravity feed of shredded waste into the decontamination chamber. The advancement unit in the illustrated embodiment comprises an auger 614, such as a screw auger, that is received within an elongated pipe 616. A motor 617 is coupled to the auger through appropriate gear reduction apparatus (not shown) and is operable, preferably in accordance with control input received from control electronics 220–230, to direct under positive pressure material from the shredder assembly 550 to the inlet 215 of the decontamination chamber 202". A motorized valve 620 is provided adjacent to the chamber inlet to seal the inlet prior to operation of the waste processing system in the manner that will be described below. Preferably, operation of the valve 620 is governed by the control electronics and software discussed previously, thereby minimizing the opportunity for human error in operation of the system.

In the illustrated embodiment, a heat jacket 624 is provided which surrounds the exterior of the decontamination chamber so as to be in heat exchange relationship therewith. The heat jacket 624 receives steam or heated water from a condensing unit 628 that is operable to receive and process steam from an existing high pressure steam line 630. Such high pressure lines are commonly provided in manufacturing facilities, hospitals and laboratories in which the processing system of the present invention is particularly adapted for use. High pressure steam is typically maintained at a pressure of about 125 psi and at a temperature of about 325° F. (163° C.). Fluid condensed by the condensing unit is delivered to the heat jacket 624 through fluid line 631. In a preferred aspect of the invention, the condensing unit 628 is operable to condense 125 psi steam to a volume of about 4 gallons in a period of about one minute in order to supply the heat jacket 624 with a sufficient quantity of heat energy to elevate and maintain the temperature of the waste contents of the decontamination chamber at a temperature in the range of from about 270° F. (132° C.) to about 275° F. (135° C.). The temperature of the fluid within fluid line 631 is monitored by a suitable temperature sensor (not shown). A valve 632 mounted within fluid line 631 is operable, preferably automatically in accordance with control electronics programming, to terminate the flow of fluid from the condensing unit 628 to the heat jacket in instances where the temperature of the fluid exceeds a prescribed maximum temperature. Excess condensed fluid can be directed through outlet line 635 to a boiler or other suitable high temperature fluid reservoir (not shown). An auxiliary condensing unit 636, which is in fluid communication with condensing unit 628 by way of conduit 638, can optionally be provided to further condense steam received by the condensing unit 628. Output from the auxiliary condensing unit 636 can be directed through output line 640 to the high temperature fluid reservoir.

Operation of the waste processing system illustrated in FIG. 11 is as follows. Bulk waste material is received within the hopper 562 of the shredder assembly 550. Preferably, the shredder unit 566 is activated prior to delivery of the waste material into the hopper. This can be accomplished by, for example, providing a trip switch or similar sensor (not shown) at the hopper lid 574 that is operable to activate the motor upon elevation of the lid beyond a prescribed height. Waste received within the hopper is directed to the shredder unit 566, where it is shredded incident to preliminary waste handling. Shredded waste is directed to the decontamination chamber 202' under the positive influence of the waste advancement unit 612. Operation of the waste advancement unit, shredder unit 566 and exhaust fan 582 can advantageously be coupled to a single event, such as opening of the hopper lid 574, by the provision of appropriate trip switches and the like.

Waste material is received within the decontamination chamber 202' and mixed with a suitable processing fluid until a fluid level sensor associated with the decontamination chamber signals to the control electronics that the chamber is full. Upon filling of the chamber 202", power to the shredder assembly 566 and auger assembly 612 is terminated, and the valve 620 at the decontamination chamber inlet 215 is closed. The processing fluid and waste mixture that is received within the decontamination chamber is processed by the chopper/pump 204 in the manner described previously in connection with the embodiment depicted in FIG. 10. In instances where water is to be used as the processing fluid, heated water from one or both of the condensing units 628 and 636 can be directed to the interior of the decontamination chamber 202" through appropriate supply conduits (not shown). Suitable processing fluids are those which are relatively inexpensive, plentiful, feature boiling points at standard pressure in excess of the 270° F. to 275° F. (132° C.–135° C.) operating environment that is necessary to accomplish sterilization during a processing cycle of approximately six minutes. Upon completion of a processing cycle, the fluid-waste mixture is cooled in the manner described in connection with the embodiment depicted in FIG. 10, and the waste solids are filtered and optionally dried mad compacted prior to disposal. The liquid component of the fluid-waste mixture can be passed into a sanitary sewer or recovered, at least in part, for reuse in a subsequent waste processing cycle. Periodically, disinfectant is applied from the hopper cleansing system 584 to the interior of the hopper 562 to cleanse and disinfect the interior of the hopper 562, shredder unit 550 and material advancement unit (auger) 612, as none of the surfaces of these assemblies is exposed to heated processing fluid. Operation of the hopper cleansing system 584 is preferably tied to operation of the shredder exhaust fan 582 to ensure proper control of airborne contaminants.

The system operation is similar for the removal of coatings from waste coated plastic material and for the dissolution of water soluble polymeric or fibrous waste material. Since lower operating temperatures are used for treating the water soluble polymeric or fibrous waste material, the system does not need to be pressurized as described above for the biological neutralization of medical waste. The system can operate under the pressure generated within the closed system by the heated fluid.

While the invention has been disclosed in this application by reference to the details of the preferred embodiments of the invention, it is to be understood that the disclosure is intended in an illustrative rather than a limiting sense, as it is contemplated that modifications will readily occur to those skilled in the art, within the spirit of the invention and the scope of the appended claims.

What is claimed is:

1. A process for removing a coating from plastic waste material having a coating, comprising the steps of:
   providing plastic waste material to be processed;
   grinding the waste material to form particles of predetermined maximum size;
   mixing the ground waste material with a liquid and circulating the liquid and entrained waste material through a closed waste processing circuit; and
   heating and circulating the mixture of liquid and waste material to a temperature sufficient to remove said coating from the plastic waste material.

2. The process according to claim 1, further comprising the step of discharging the processed waste material, and wherein waste solids of a minimum prescribed size are separated from the mixture of liquid and waste material from the closed waste processing circuit prior to discharge.

3. The process according to claim 1, further comprising the step of discharging the processed waste material, and wherein the temperature of the processed waste material from the closed waste processing circuit is reduced following waste processing and prior to discharge.

4. The process according to claim 3, further comprising the step of generating a record of the mixture of liquid and waste material temperature and processing time.

5. The process according to claim 4, wherein said record is rendered in tangible form.

6. The process according to claim 1, further comprising the step of inhibiting access to the waste material until a prescribed level of coating removal has been achieved.

7. The process according to claim 1, further comprising the step of generating human intelligible indicia indicative of the status of waste processing.

8. The process of claim 1, wherein said temperature sufficient to remove the coating is between 270° F. and 450° F.

9. A process for dissolving water soluble polymeric or fibrous waste material comprising the steps of:
   providing water soluble polymeric or fibrous waste material to be processed;
   grinding the waste material to form particles of predetermined maximum size;
   mixing the ground waste material with a liquid and circulating the liquid and entrained waste material through a closed waste processing circuit; and
   heating and circulating the mixture of liquid and waste material to a temperature sufficient to dissolve said water soluble polymeric or fibrous waste material.

10. The process according to claim 9, further comprising the step of discharging the processed waste material, and wherein waste solids of a minimum prescribed size are separated from the mixture of liquid and waste material from the closed waste processing circuit prior to discharge.

11. The process according to claim 9, further comprising the step of discharging the processed waste material, and wherein the temperature of the processed waste material from the closed waste processing circuit is reduced following waste processing and prior to discharge.

12. The process according to claim 11, further comprising the step of generating a record of the mixture of liquid and waste material temperature and processing time.

13. The process according to claim 12, wherein said record is rendered in tangible form.

14. The process according to claim 9, further comprising the step of inhibiting access to the waste material until a prescribed level of dissolution has been achieved.

15. The process according to claim 9, further comprising the step of generating human intelligible indicia indicative of the status of waste processing.

16. The process according to claim 9, wherein said temperature sufficient to dissolve said water soluble polymeric or fibrous material is between 175° F. and 250° F.

17. The process according to claim 9, wherein said temperature sufficient to dissolve said water soluble polymeric or fibrous material is between 185° F. and 205° F.

* * * * *